US008999388B2

(12) United States Patent
Lim et al.

(10) Patent No.: US 8,999,388 B2
(45) Date of Patent: Apr. 7, 2015

(54) DUAL DRUG DOSAGE FORMS WITH IMPROVED SEPARATION OF DRUGS

(71) Applicant: Depomed, Inc., Newark, CA (US)

(72) Inventors: Jong Lim, San Jose, CA (US); John N. Shell, Lincoln, CA (US); Jenny Louie-Helm, Fremont, CA (US)

(73) Assignee: Depomed, Inc., Newark, CA (US)

( * ) Notice: Subject to any disclaimer, the term of this patent is extended or adjusted under 35 U.S.C. 154(b) by 0 days.

(21) Appl. No.: 14/199,972

(22) Filed: Mar. 6, 2014

(65) Prior Publication Data

US 2014/0186515 A1 Jul. 3, 2014

Related U.S. Application Data

(62) Division of application No. 13/530,631, filed on Jun. 22, 2012, now Pat. No. 8,685,450, which is a division of application No. 10/623,481, filed on Jul. 18, 2003, now abandoned.

(51) Int. Cl.
*A61K 9/22* (2006.01)
*A61K 9/24* (2006.01)
*A61K 31/00* (2006.01)
*A61K 45/06* (2006.01)
*A61K 9/20* (2006.01)
*A61K 31/155* (2006.01)
*A61K 31/40* (2006.01)
*A61K 31/4015* (2006.01)
*A61K 31/4415* (2006.01)
*A61K 9/00* (2006.01)

(52) U.S. Cl.
CPC ............... *A61K 9/209* (2013.01); *A61K 31/00* (2013.01); *A61K 45/06* (2013.01); *A61K 9/2027* (2013.01); *A61K 9/2031* (2013.01); *A61K 9/2054* (2013.01); *A61K 31/155* (2013.01); *A61K 31/40* (2013.01); *A61K 31/4015* (2013.01); *A61K 31/4415* (2013.01); *A61K 9/0065* (2013.01)

(58) Field of Classification Search
CPC ......... A61K 9/00; A61K 9/20; A61K 9/2001; A61K 9/2054; A61K 9/2086; A61K 9/209; A61K 9/2095
USPC .......................................... 424/464, 489, 470
See application file for complete search history.

(56) References Cited

U.S. PATENT DOCUMENTS

| | | | |
|---|---|---|---|
| 4,024,175 A | 5/1977 | Satzinger et al. | |
| 4,292,299 A | 9/1981 | Suzuki et al. | |
| 4,786,503 A | 11/1988 | Edgren et al. | |
| 4,786,505 A | 11/1988 | Lovgren et al. | |
| 4,891,230 A | 1/1990 | Geoghegan et al. | |
| 4,894,476 A | 1/1990 | Butler et al. | |
| 5,007,790 A | 4/1991 | Shell | |
| 5,085,865 A | 2/1992 | Nayak | |
| 5,162,117 A | 11/1992 | Stupak et al. | |
| 5,213,807 A | 5/1993 | Chemburkar et al. | |
| 5,549,913 A | 8/1996 | Colombo et al. | |
| 5,582,837 A | 12/1996 | Shell | |
| 5,681,583 A | 10/1997 | Conte et al. | |
| 5,780,057 A | 7/1998 | Conte et al. | |
| 5,837,379 A | 11/1998 | Chen et al. | |
| 5,861,173 A | 1/1999 | Nishiioka et al. | |
| 5,922,769 A | 7/1999 | Barelli et al. | |
| 5,972,389 A | 10/1999 | Shell et al. | |
| 6,011,049 A | 1/2000 | Whitcomb | |
| 6,031,004 A | 2/2000 | Timmins et al. | |
| 6,054,482 A | 4/2000 | Augart et al. | |
| 6,056,977 A | 5/2000 | Bhagwat et al. | |
| 6,074,674 A | 6/2000 | Jay et al. | |
| 6,099,862 A | 8/2000 | Chen et al. | |
| 6,126,969 A | 10/2000 | Shah et al. | |
| 6,153,632 A | 11/2000 | Rieveley | |
| 6,159,499 A | 12/2000 | Seth | |
| 6,171,618 B1 * | 1/2001 | Johnson et al. ............... 424/472 |
| 6,183,777 B1 | 2/2001 | Chen et al. | |
| 6,183,778 B1 | 2/2001 | Conte et al. | |

(Continued)

FOREIGN PATENT DOCUMENTS

| | | |
|---|---|---|
| EP | 0795324 A2 | 9/1997 |
| EP | 0665744 | 12/1997 |
| EP | 0598309 B1 | 1/1998 |
| EP | 1112738 | 7/2001 |
| GB | 1330829 | 9/1973 |
| WO | WO 94/06416 A1 | 3/1994 |
| WO | WO 94/09761 A1 | 5/1994 |
| WO | WO 95/20946 A1 | 8/1995 |
| WO | WO 96/26718 A2 | 9/1996 |
| WO | WO 98/55107 A1 | 12/1998 |
| WO | WO 00/23045 A1 | 4/2000 |
| WO | WO 00/74655 A2 | 12/2000 |
| WO | WO 03/020243 A1 | 3/2003 |
| WO | WO 03/066028 A1 | 8/2003 |

OTHER PUBLICATIONS

Baichwal & Neville, "Culturing innovation and enhancing medications using oral drug delivery", Drug Del Tech., vol. 2, No. 3, pp. 65-68 (2002).

(Continued)

*Primary Examiner* — Michael G Hartley
*Assistant Examiner* — Micah-Paul Young
(74) *Attorney, Agent, or Firm* — McDermott Will & Emery LLP

(57) ABSTRACT

Drug tablets that include a prolonged-release core and an immediate-release layer or shell are prepared with a thin barrier layer of drug-free polymer between the prolonged-release and immediate-release portions of the tablet. The barrier layer is penetrable by gastrointestinal fluid, thereby providing full access of the gastrointestinal fluid to the prolonged-release core, but remains intact during the application of the immediate-release layer, substantially reducing or eliminating any penetration of the immediate-release drug into the prolonged-release portion.

17 Claims, No Drawings

(56) References Cited

U.S. PATENT DOCUMENTS

| | | | |
|---|---|---|---|
| 6,194,000 | B1 | 2/2001 | Smith et al. |
| 6,211,205 | B1 | 4/2001 | Ikeda et al. |
| 6,248,355 | B1 | 6/2001 | Seth |
| 6,270,797 | B1 | 8/2001 | Gidwani et al. |
| 6,274,608 | B1 | 8/2001 | Sauerberg et al. |
| 6,294,690 | B1 | 9/2001 | Deering et al. |
| 6,372,255 | B1 | 4/2002 | Saslawski et al. |
| 6,475,521 | B1 | 11/2002 | Timmins et al. |
| 6,558,701 | B2 | 5/2003 | Bartholomaeus et al. |
| 6,682,795 | B1 | 1/2004 | Gilliard et al. |
| 6,780,436 | B1 | 8/2004 | Lopez-Cabrera-Cabera et al. |
| 6,814,979 | B2 | 11/2004 | Rudnic et al. |
| 2001/0018070 | A1 | 8/2001 | Shell et al. |
| 2001/0036478 | A1 | 11/2001 | Adjei et al. |
| 2002/0128251 | A1 | 9/2002 | Storm et al. |

OTHER PUBLICATIONS

Daily Med, Current Medication Information, "Oxycodone Hydrochloride and Ibuprofen (Oxycodone hydrochloride and ibuprofen) tablet", Watson Laboratories, Inc., Online article downloaded from URL: http://dailymed.nlm.nih.gov/dailymed/archives/fdaDrugInfo.cfm?archiveid=6338, 2 pages, (2007).
Eudragit®, An Evonik product, "EUDRAGIT° NE 30 D" Evonik Industries AG, Online article downloaded from URL: http://eudragit.evonik.com/product/eudragit/Documents/evonik-specification-eudragit-ne-30-d.pdf, 5 pages, 2012.
Halsas et al., "Effect of different combinations of hydroxypropylmethyl cellulose on bioavailability of ibuprofen from press-coated time-controlled tablets", S.T.P. Pharma Sci., vol. 8, No. 3, pp. 155-161 (1998).
Handbook of Pharmaceutical Excipients, Fifth Edition, "Hypromellose", Rowe et al.. Ed., Pharmaceutical Press, Publications division of the Royal Pharmaceutical Society of Great Britain, 1 Lambeth High Street, London SE1 7JN, UK, and the American Pharmacists Association, 2215 Constitution Avenue, NW, Washington, DC 20037-2985, USA, pp. 346-347 (2006).
International Search Report from related PCT Patent Application No. PCT/US2004/022554, mailed Jan. 7, 2005, application now published as International Publication No. WO 2005/009413 on Feb. 3, 2005.
Lee, "Controled release of dual drug-loaded hydroxyprpyl methylcellulose matrix tablet using drug-containing polymeric coatings", Int. J. Pharm., vol. 188, pp. 71-80 (1999).
"Methocel cellulose ethers in aqueous systems for tablet coating", Dow Chemical Company, pp. 1-32 (2002).
Siepmann et al., "Modeling of drug release from delivery systems based on hydroxypropyl methylcellulose (HPMC)", Adv. Drug Del. Rev., pp. 139-157 (2001).
Sirkia et al., "Use of hydrophilic polymers to control drug release from press-coated oxybutynin hydrochloride tablets", S.T.P. Pharma Sci., vol. 3, No. 6, pp. 453-458 (1993).
Sirkia et al., "Biopharmaceutical evaluation of new prolonged-release press-coated ibuprofen tablets containing sodium alginate to adjust drug release", Int. J. Pharm., vol. 107, pp. 179-187 (1994).
Sirkia et al., "Development and biopharmaceutical evaluations of a new press-coated prolonged-release salbutamol sulphate tablet in man", European J. Pharm. Sci., vol. 1, pp. 195-201 (1994).
Supplemental European Search Report for European Patent Application No. 04778191.9, 8 pgs., Mailed Jun. 7, 2010.

\* cited by examiner

DUAL DRUG DOSAGE FORMS WITH IMPROVED SEPARATION OF DRUGS

CROSS-REFERENCE TO RELATED APPLICATION

This application is a divisional of U.S. application Ser. No. 13/530,631, filed Jun. 22, 2012, now allowed, which is a divisional of U.S. application Ser. No. 10/623,481, filed Jul. 18, 2003, now abandoned, each of which is incorporated herein by reference in its entirety.

BACKGROUND OF THE INVENTION

1. Field of the Invention

This invention is in the field of pharmacology, and relates to drug dosage forms that are designed to deliver drugs concurrently in both immediate-release and prolonged-release delivery profiles.

2. Description of the Prior Art

Certain pharmacological therapies either require or benefit from the sequential administration of two or more drugs. While this can be accomplished if the administration is done according to a strict time schedule, many patients have difficulty complying with such a schedule without the assistance of a medical professional. Some therapies involve only an immediate but rapidly declining high-level dosage and a prolonged dosage at a low or moderate level, the two dosages being either of the same drug or of a different drug. Even two-dosage therapies such as these however can be troublesome to maintain if a separate administration is needed for each dosage. Certain pharmaceutical formulations have therefore been developed that combine both functions into a single dosage form. This simplifies the therapy and reduces or eliminates the chances of improper administration.

Many unitary dosage forms have been proposed that combine an immediate release drug with a prolonged release drug by placing the drugs in different layers of a tablet or by placing one drug in a quickly-dissolving or quickly-dispersing shell that surrounds the slowly dissolving or swellable core that contains the other drug. The immediate-release layer or shell is typically formed by coating the pre-formed prolonged-release portion with a solution or a suspension of the immediate-release drug and a polymer and then allowing the liquid carrier in which the drug and polymer are dissolved or suspended to evaporate, leaving a solid dry outer layer. In some cases, however, the liquid carrier tends to cause swelling of the outer surface of the prolonged-release portion. As the prolonged-release matrix swells, some of the drug intended for immediate release enters the prolonged-release matrix. When the immediate-release drug is applied as a suspension of particles, the particles tend to become trapped in the prolonged-release matrix. High-potency drugs that are intended for immediate release are therefore retained rather than released. The problem can be particularly acute when the drug is insoluble or of low solubility, since unintended retention of the drug in the prolonged-release portion can significantly reduce the amount of the drug that is available for absorption into the patient's bloodstream.

SUMMARY OF THE INVENTION

It has now been discovered that a drug dosage form that includes a prolonged-release core and an immediate-release layer or shell can be manufactured in a manner that reduces or prevents any migration of drug from the immediate-release portion into the prolonged-release portion, by interposing a thin protective layer of drug-free polymer between the prolonged-release and immediate-release portions. The protective layer is penetrable by, or dissolved in, water or gastrointestinal fluid, thereby providing full access of the gastrointestinal fluid to the prolonged-release core. The protective layer remains intact however during the application of the immediate-release layer, substantially reducing or eliminating any penetration by the immediate-release drug. The protective layer thereby allows immediate release of the entire dose of drug in the outer layer. The inclusion of the protective layer also serves to prevent interaction of the prolonged-release and immediate-release drugs, which is of value in cases where interaction between the two drugs may be detrimental to the activity of either or both of the drugs.

This discovery extends to dosage forms in which the immediate-release layer is applied either as a solution of the drug in an aqueous or organic solvent or as a suspension of solid particles of the drug in an aqueous or organic liquid carrier. In most cases, the liquid carrier also contains dissolved, dispersed or suspended polymer to assist in the formation of an immediate release coating. The discovery is of particular interest as applied to immediate-release layers applied as suspensions of solid particles, but also those that are applied as solutions. A disclosure of certain dosage forms in which the immediate-release layer is prepared from particulate suspensions is found in commonly owned, co-pending U.S. patent application Ser. No. 10/066,146 (now U.S. Pub. No. 2003/0147952), filed Feb. 1, 2002, entitled "Manufacture of Oral Dosage Forms Delivering Both Immediate-Release and Sustained-Release Drugs," Lim et al., inventors, the contents of which are incorporated herein by reference.

DETAILED DESCRIPTION OF THE INVENTION AND PREFERRED EMBODIMENTS

The dosage forms of this invention are designed for oral ingestion, and the prolonged-release portion of the dosage form is one that delivers its drug to the digestive system continuously over a period of time of at least an hour and preferably several hours. The drug is retained in a matrix or supporting body of pharmaceutically inert solid, and the prolonged delivery rate can be achieved by using a matrix that allows the gastrointestinal fluid to permeate the matrix and leach out the drug (i.e., allow the drug to diffuse out from the matrix as the drug slowly dissolves in the permeating fluid), or a matrix that slowly dissolves or erodes to expose the drug to the gastrointestinal fluid, or one that dissolves or erodes while allowing the gastrointestinal fluid to permeate. The delivery rate is preferably slow enough that at least about 40% of the drug remains unreleased one hour after ingestion, more preferably at least about 60% and most preferably at least about 80%. In most cases, the drug will be substantially all released within about ten hours and preferably within about eight hours, and in many cases, the matrix supporting the drug will remain substantially intact until all of the drug is released. "Substantially intact" in this sense means that the matrix retains at least most of its size and shape rather than dissolving or disintegrating into fragments. In this specification, the term "prolonged-release" is equivalent to the terms "controlled-release" and "sustained-release" as used in the prior art.

In certain preferred embodiments of the invention, the supporting matrix in the prolonged-release portion of the tablet is a material that swells upon contact with gastrointestinal fluid to a size that is large enough to promote retention in the stomach while the subject is in the digestive state, which is also referred to as the postprandial or "fed" mode. The "fed"

mode is one of two modes of activity of the stomach that differ by their distinctive patterns of gastroduodenal motor activity. The "fed" mode is induced by food ingestion and begins with a rapid and profound change in the motor pattern of the upper gastrointestinal (GI) tract. The change consists of a reduction in the amplitude of the contractions that the stomach undergoes and a reduction in the pyloric opening to a partially closed state. The result is a sieving process that allows liquids and small particles to pass through the partially open pylorus while indigestible particles that are larger than the pylorus are retropelled and retained in the stomach. This process causes the stomach to retain particles that are greater than about 1 cm in size for about 4 to 6 hours. The prolonged-release matrix in these embodiments of the invention is therefore selected as one that swells to a size large enough to be retropelled and thereby retained in the stomach, causing the prolonged release of the drug to occur in the stomach rather than in the intestines.

Disclosures of oral dosage forms that swell to sizes that will prolong the residence time in the stomach are found in U.S. Pat. No. 5,007,790 ("Sustained-Release Oral Drug Dosage Form," Shell, inventor; Apr. 16, 1991); U.S. Pat. No. 5,582,837 ("Alkyl-Substituted Cellulose-Based Sustained-Release Oral Drug Dosage Forms," Shell, inventor; Dec. 10, 1996); U.S. Pat. No. 5,972,389 ("Gastric-Retentive Oral Drug Dosage Forms for the Controlled Release of Sparingly Soluble Drugs and Insoluble Matter," Shell et al., inventors; Oct. 26, 1999); International (PCT) Patent Application WO 98/55107 ("Gastric-Retentive Oral Drug Dosage Forms for Controlled Release of Highly Soluble Drugs," Shell et al., inventors; publication date Dec. 10, 1998); United States Patent Application Publication No. US 2001/0018707 A1 ("Extending the Duration of Drug Release Within the Stomach During the Fed Mode," Shell et al., inventors, publication date Aug. 30, 2001); and International (PCT) Patent Application WO 96/26718 ("Controlled Release Tablet," Kim, inventor: publication date Sep. 6, 1996). Each of the documents cited in this paragraph is incorporated herein in its entirety.

In general, gastric-retentive (swellable) matrices contain binders that are waterswellable polymers, and suitable polymers are those that are non-toxic, that swell in a dimensionally unrestricted manner upon imbibition of water, and that release the drug gradually over time. Examples of polymers meeting this description are:

- cellulose polymers and substituted cellulose polymers, including alkyl-substituted, hydroxyalkyl-substituted, and carboxyalkyl-substituted celluloses, specific examples being, although not limited to, hydroxymethyl cellulose, hydroxyethyl cellulose, hydroxypropyl cellulose, hydroxypropylmethyl cellulose, and carboxymethyl cellulose, and microcrystalline cellulose polysaccharides and substituted polysaccharides (with substituents such as those listed above)
- poly(alkylene oxide)s
- chitosan
- poly(vinyl alcohol)
- xanthan gum
- maleic anhydride copolymers
- poly(vinyl pyrrolidone)
- starch and starch-based polymers
- maltodextrins
- poly (2-ethyl-2-oxazoline)
- poly(ethyleneimine)
- polyurethane hydrogels
- crosslinked poly(acrylic acid)s and substituted crosslinked poly(acrylic acid)s (with substituents such as those listed above)

Further examples are copolymers of the polymers listed above, including block copolymers and graft polymers. Specific examples of copolymers are PLURONIC and TECTONIC®, which are polyethylene oxide-polypropylene oxide block copolymers available from BASF Corporation, Chemicals Div., Wyandotte, Mich., USA. Further examples are hydrolyzed starch polyacrylonitrile graft copolymers, commonly known as "Super Slurper" and available from Illinois Corn Growers Association, Bloomington, Ill., USA. Particularly preferred polymers are poly(ethylene oxide), hydroxypropyl methyl cellulose, and combinations of poly(ethylene oxide) and hydroxypropyl methyl cellulose.

The immediate-release portion of the dosage form is either a coating applied or deposited over the entire surface of a unitary prolonged-release core, or a single layer of a tablet constructed in two or more layers, one of the other layers being the prolonged-released portion. Immediate release of the drug from the immediate-release layer is achieved in any of a variety of ways. One example is by placing the drug in a layer or coating that is sufficiently thin to allow fast penetration by gastrointestinal fluid which then leaches the drug at a rapid rate. Another example is by incorporating the drug in a mixture that includes a supporting binder or other inert material that dissolves readily in gastrointestinal fluid, releasing the drug as the material dissolves. A third is the use of a supporting binder or other inert material that rapidly disintegrates into fine particles upon contact with gastrointestinal fluid, with both the binder particles and the drug quickly dispersing into the fluid. Examples of materials that rapidly disintegrate and disperse are lactose and microcrystalline cellulose. Hydroxypropyl methyl cellulose is a component that can serve both as a suspending agent and as a binder.

The dosage forms of this invention include those in which the same drug is used in both the immediate-release and the prolonged-release portions as well as those in which one drug is formulated for immediate release and another drug, different from the first, is formulated for prolonged release. In cases involving the same drug, the invention serves to assure that the full immediate-release dosage of the drug is achieved rather than loss of the immediate-release effect. In cases involving one drug for immediate release and a different drug for prolonged release, the invention prevents the two drugs from commingling to the detriment of one or the other and assures that the full immediate-release dosage is achieved rather than a portion being lost to the prolonged-release region of the dosage form.

This invention extends to both high-solubility and low-solubility drugs, as well as drugs that are combined with an additive that serves to solubilize the drug or suspend it in a liquid carrier. Any of these drugs can be used as the immediate-release drug. Immediate-release drugs that are either sparingly soluble or insoluble in water, regardless of the solubility of the prolonged-release drug, are of particular interest in certain embodiments of this invention. The immediate-release drug in these dosage forms is of sufficiently low solubility that it remains a solid particle during the preparation of the dosage form. In certain embodiments of the invention, the dispersing medium is water or an aqueous solution that may contain other components. The term "at most sparingly soluble" as used herein denotes a drug having a solubility in water at 25° C. that is generally less than 2% by weight, preferably less than 0.5% by weight. When the drug is in particulate form, the preferred particle size is equal to or less than about 25 microns in diameter, more preferably equal to or less than about 10 microns in diameter, still more preferably within the range of from about 0.3 micron to about 10 microns in diameter, and most preferably with the range of from about 1 micron to about 5 microns in diameter, all on a weight-average basis.

This invention is also applicable to dosage forms in which the dispersing medium for the immediate-release drug is an organic liquid, such as for example, ethanol, hexanes, chloroform, carbon tetrachloride, or dimethyl sulfoxide. An advantage of the use of a relatively volatile organic liquid is a rapid rate of evaporation to leave a dry coating. Organic liquids are also useful for drugs that are unstable in aqueous solutions.

The intermediate layer of drug-free polymer that serves as a barrier to migration of the immediate-release drug into the prolonged-release matrix during application of the immediate-release layer can be applied over the prolonged-release segment as a solution or a suspension of the polymer, in the same manner by which the immediate-release drug is applied over the barrier layer. The polymer is one that is penetrable by gastrointestinal fluid and can be either soluble in gastrointestinal fluid or insoluble but erodible upon contact with gastrointestinal fluid, or simply insoluble. The polymer can also be one that swells upon imbibition of water in the same manner as the prolonged-release matrix. Polymers that are soluble or erodible in gastrointestinal fluid will be those of which a sufficient amount remains during the formation of the immediate-release layer to serve as a barrier until the immediate-release layer is fully applied and dried. The ability of the polymer to do this may vary with the thickness of the layer, the molecular weight of the polymer and, for swellable polymers, the swelling characteristics of the polymer. A small degree of swellability may be favorable to accommodate any swelling of the prolonged-release matrix that may occur during the application of the polymer over the matrix without creating fissures in the polymer layer.

The same polymers listed above for use as the matrix in the prolonged-release portion of the dosage form can be used in the barrier layer. In many cases, it will be beneficial to use the same polymer as both the prolonged-release matrix and the barrier layer, for purposes of compatibility between the core and the barrier. When the matrix is a mixture of polymers, the barrier polymer can be one or more of the polymers of the mixture. When the same polymer is used in both regions, a form of the polymer having a lower molecular weight is preferably used in the barrier layer since a polymer of lower molecular weight will more readily release the immediate-release drug to the gastric environment. Preferred polymers for use in forming the film are poly(ethylene oxide) hydroxypropyl methyl cellulose, poly(vinyl alcohol), combinations of poly(ethylene oxide) and hydroxypropyl methyl cellulose, and combinations of poly(vinyl alcohol) and poly(ethylene oxide).

As noted above, the amount of the polymer in the intermediate layer may affect the barrier characteristics of the layer but it may also affect the performance of the dosage form upon ingestion, i.e., the intermediate layer may further lower the rate of release of drug from the prolonged-release portion once the prolonged-release portion is exposed. In general, however, the amount can vary widely. In most cases, best results will be achieved when the weight ratio of the polymer in the intermediate layer to the prolonged-release core is from about 0.005:1 to about 0.2:1, preferably from about 0.01:1 to about 0.1:1, and most preferably from about 0.01:1 to about 0.08:1.

The immediate-release drug can thus be deposited as a suspension or a solution over a unitary core of the prolonged-release drug coated with the intermediate layer. Deposition can be achieved by coating techniques commonly used in the pharmaceutical formulation art, such as spraying, pan coating, and the like. Alternatively, the immediate-release drug can be combined with particles of a binding matrix and compressed over a preformed layer of the prolonged-release drug to form a layered tablet. In either case, the immediate-release coating or layer separates relatively quickly from the remainder of the tablet after ingestion, leaving the remainder intact.

The choice of drugs for use in either the prolonged-release or immediate-release portions of the dosage form is not critical to the invention, and many different types of drugs can be used. The selection will depend on the condition to be treated, the therapy being sought and the needs of the particular patient. Drugs of high solubility in water as well as drugs of low solubility can occupy either the prolonged-release or immediate-release portions. Examples of high-solubility drugs are metformin hydrochloride, vancomycin hydrochloride, captopril, lisinopril, erythromycin lactobionate, ranitidine hydrochloride, sertraline hydrochloride, ticlopidine hydrochloride, baclofen, amoxicillin, cefuroxime axetil, cefaclor, clindamycin, levodopa, doxifluridine, tramadol, fluoxetine hydrochloride, bupropion, potassium chloride, and esters of ampicillin. Examples low solubility drugs are saguinavir, ritonavir, nelfinavir, thiamphenicol, ciprofloxacin hydrochloride, calcium carbonate, clarithromycin, azithromycin, ceftazidime, acyclovir, ganciclovir, cyclosporin, digoxin, paclitaxel, iron salts, topiramate, ketoconazole, and sulfonylureas such as glimepiride, glyburide, and glipizide. Other drugs suitable for use will be apparent to those skilled in the art.

One of the many areas of interest for this invention are combinations of a diuretic and either an angiotensin converting enzyme inhibitor or an angiotensin H antagonist. Preferably, the angiotensin converting enzyme inhibitor or angiotensin II antagonist will occupy the immediate-release portion and the diuretic the prolonged-release portion, although for certain patients a more appropriate dosage form may be one in which the diuretic occupies the immediate-release portion and the angiotensin converting enzyme inhibitor or angiotensin II antagonist occupies the prolonged-release portion. Lisinopril is an example of an angiotensin converting enzyme inhibitor, and examples of other similar drugs are enalapril, captopril, fosinopril, quinapril, ramipril, and benazepril. Losartan is an example of an angiotensin II antagonist, and examples of other drugs of this class that might be used are valsartan, candesartan, irbesartan, telmisartan, and eprosartan. Loop diuretics, i.e., those acting on the sodium-potassium symporter in the ascending loop of Henle in the kidneys to decrease the rate of readsorption of water and sodium, are also of particular interest. Examples are furosemide, torsemide, ethacrynic acid, and bumetanide. Thiazides and thiazide-like diuretics are believed to act primarily on the sodium-potassium symporter in the distal convoluted tubule. Examples of this type of diuretic are chlorothiazide and its sodium, salt, bendoflumethazide, hydroflumethazide, trichlorthiazide, chlorthalidone, indapamide, metolazone, quinethazone and hydrochlorothiazide. Potassium-sparing diuretics act in the late distal tubule and collecting duct. Examples are amiloride hydrochloride and triamterene.

Another class of combinations of particular interest is metformin hydrochloride as the prolonged-release drug, and a glitazone as the immediate-release drug. Examples of glitazones are rosiglitazone (maleate), pioglitazone, and troglitazone. Yet another class of combinations is pyridoxine hydrochloride as the immediate-release drug, and a statin as the prolonged-release drug. Examples of statins are atorvastatin, simvastatin, pravastatin, lovastatin, cerivastatin, rosuvastatin, and fluvastatin. Of these, atorvastatin and simvastatin are preferred.

The amounts of drugs in the immediate-release and prolonged-release portions can vary widely, depending on the potencies of the drugs and the desired dosage rates. Amounts of either drug in a single dosage form can range from about 1 mg to about 1,000 mg. In most cases the appropriate amounts will range from about 5 mg to about 500 mg. This paragraph sets forth a number of examples, others of which will be readily apparent to those skilled in the formulation and prescription of these drugs. In dosage forms that include furosemide, for example, or other drugs of similar potency as prolonged-release diuretics, a preferred dosage range of the diuretic is 10-120 mg. Lisinopril when present is preferably in an amount of about 5 mg to about 40 mg. Losartan when present is preferably in an amount of about 10 mg to about 100 mg. Loop diuretics when present are preferably in an amount of about 5 mg to about 200 mg. When metformin hydrochloride is used as the prolonged-release drug with a glitazone in the immediate-release layer, a 500-mg metformin hydrochloride dose, for example, can be accompanied by a 4-8-mg dose of a glitazone such as rosiglitazone maleate. In some cases, the amount of drug in the immediate-release portion will exceed the amount in the prolonged-release portion. Dosage forms for example that contain pyridoxine hydrochloride as the immediate-release drug and a statin such as atorvastatin or simvastatin as the prolonged-release drug may contain 100-200 mg of pyridoxine hydrochloride and either 20-40 mg of atorvastatin or 40-80 mg of simvastatin.

100241 Preferred dosage forms in accordance with this invention are tablets, and the size, shape, and dimensions of the tablets are not critical to the invention. In embodiments where a swellable matrix is used, the tablet upon swelling is preferably large enough to reach the dimensions that will cause it to be retained in the stomach during the fed mode. The tablet may be circular or elongated. An elongated tablet may be 18 to 22 mm in length, 6.5 to 10 mm in width, and 6.2 to 7.5 mm in height. A specific example is one that is 20 mm in length, 6.7 mm in width, and 6.4 mm in height. Again, these are merely examples; the shapes and sizes can be varied considerably.

Tablets in accordance with this invention can be prepared by conventional mixing, comminution, and tableting techniques that are well known in the pharmaceutical industry. The prolonged-release portion can for example be fabricated by direct compression in punches and dies fitted to a rotary tablet press, or by ejection or compression molding, granulation followed by compression, or the formation of a paste that is then extruded into a mold or into an extrudate which is then cut into short lengths. The intermediate (barrier) layer can be applied as a coating over the prolonged-release portion by spraying, dipping, or pan-coating, and the immediate-release portion can be applied as a coating over the intermediate layer by the same techniques, or as an additional layer by tableting or compression in the same manner as the prolonged-release portion.

The following examples, both actual and prophetic, are offered for purposes of illustration and are not intended to limit the scope of the invention.

EXAMPLE 1

This example illustrates the preparation of tablets in accordance with this invention that contain 500 mg metformin hydrochloride as the prolonged-release component and 1 mg glimepiride as the immediate-release component.

Pre-formed tablets containing 500 mg of metformin hydrochloride in a matrix of hydroxypropyl methyl cellulose, poly(ethylene oxide), microcrystalline cellulose, and magnesium stearate were used as a starting material. A barrier layer solution was prepared by dissolving OPADRY® YS-1-19025-A Clear ("OPADRY Clear," hydroxypropyl methyl cellulose, available from Colorcon, West Point, Pa., USA) in purified water to a concentration of 8 weight percent. This solution was sprayed onto the metformin hydrochloride tablets until the tablet weight increased by approximately 1%.

A suspension for applying the immediate-release layer was prepared by dissolving polyethylene sorbitan monooleate in purified water, dispersing glimepiride (micronized, 2-4 micron average particle size) in the solution, and adding OPADRY Clear. The resulting suspension contained 0.24% polyethylene sorbitan monooleate, 0.20% glimepiride, 7.56% OPADRY Clear, with water as the balance. The suspension was sprayed onto the barrier layer on the metformin hydrochloride tablets until the tablet weight increased by approximately 4%.

EXAMPLE 2

This example likewise illustrates the preparation of tablets in accordance with this invention that contain metformin hydrochloride as the prolonged-release component and glimepiride as the immediate-release component, but with a higher amount of glimepiride (2 mg) than Example 1.

Pre-formed metformin hydrochloride tablets identical to those used as a starting material in Example 1 were used. Likewise, an identical Opadry solution was used as the barrier layer solution. This solution was sprayed onto the tablets to achieve a weight increase of 1%.

To prepare the immediate-release layer, a suspension similar to that of Example 1 was prepared except that it contained 0.40% glimepiride rather than 0.20%. The suspension was sprayed onto the barrier layer until the tablet weight increased by approximately 4%.

EXAMPLE 3

This example illustrates the preparation of tablets in accordance with this invention that contain 500 mg metformin hydrochloride as the prolonged-release component and 2 mg glimepiride as the immediate-release component, but using a poly(vinyl alcohol)-poly(ethylene oxide) both as the barrier layer and as a component in the immediate-release layer. The poly(vinyl alcohol)-polyethylene oxide) used in the barrier layer is KOLLICOAT® IR, a product available from BASF Corporation, Chemicals Division, Wyandotte, Mich., USA.

Pre-formed metformin hydrochloride tablets identical to those used as a starting material in the preceding examples are used. The barrier layer solution is then prepared by dissolving the KOLLICOAT IR in purified water to a concentration of 8% by weight. This solution is then sprayed onto the pre-formed tablets to achieve a weight increase of 1%.

The immediate-release drug-containing coating suspension is prepared by dissolving polyethylene sorbitan monooleate in purified water, dispersing glimepiride (micronized, 2-4 micron average particle size) in the solution, adding KOLLICOAT IR, and mixing the suspension for 45-60 minutes to allow the suspension to aerate, The resulting suspension contains 0.24% polyethylene sorbitan monooleate, 0.20% glimepiride, 7.56% KOLLICOAT, with water as the balance. The suspension is sprayed onto the barrier layer until the tablet weight increases by approximately 6%.

EXAMPLE 4

This example illustrates the preparation of tablets in accordance with this invention that contain 20-40 mg atorvastatin as the prolonged-release component and 100-200 mg pyridoxine hydrochloride as the immediate-release component, again using KOLLICOAT both as the barrier layer and as a component in the immediate-release layer.

Pre-formed atorvastatin tablets containing 20 or 40 mg in a matrix of hydroxypropyl methyl cellulose, polyethylene oxide), microcrystalline cellulose, and magnesium stearate are used as a starting material. The barrier layer solution is then prepared by dissolving the KOLLICOAT IR in purified water to a concentration of 8% by weight. This solution is sprayed onto the pre-formed tablets to achieve a weight increase of 0.5-2%.

The immediate-release drug-containing coating suspension is prepared by dissolving with mixing the required amount of pyridoxine hydrochloride in purified water, then adding KOLLICOAT with further mixing and deaeration. The resulting solution is applied to the barrier layer until the tablet weight increases by approximately 6%.

The foregoing is offered primarily for purposes of illustration. It will be readily apparent to those skilled in the art that further drugs can be included, and that the shapes, components, additives, proportions, methods of formulation, and other parameters described herein can be modified further or substituted in various ways without departing from the spirit and scope of the invention.

What is claimed is:

1. A method for the manufacture of a pharmaceutical tablet which upon oral ingestion delivers a first drug by immediate release and a second drug by prolonged release defined as a release rate into gastrointestinal fluid that is slow enough to leave at least about 40% of said second drug unreleased one hour after ingestion, said method comprising:
   (a) dispersing said second drug in a solid matrix to form a unitary body which upon immersion in gastrointestinal fluid releases said second drug by prolonged release, wherein said solid matrix comprises a first polymer wherein said matrix (i) swells upon imbibition of fluid to a size that promotes retention of the dosage form in a stomach; (ii) releases substantially all of said second drug within about 10 hours upon immersion of the dosage form in fluid; and (iii) remains substantially intact until substantially all of said second drug is released;
   (b) depositing on a surface of said unitary body a polymeric film that is devoid of said first drug and said second drug, wherein said polymeric film adheres to a surface of said solid matrix and wherein said polymeric film comprises a second polymer having a molecular weight which is lower than the molecular weight of said first polymer and is dissolved in gastrointestinal fluid upon ingestion, wherein the ratio of said polymeric film to unitary body is from about 0.005:1 to about 0.2:1;
   (c) depositing over said polymeric film a fluid medium comprising said first drug and a liquid carrier that does not remove said polymeric film upon contact therewith; and
   (d) evaporating said liquid carrier from said fluid medium thus deposited to leave a solid layer containing said first drug over said unitary body, wherein said solid layer adheres to said polymeric film, and wherein said solid layer provides immediate release of said first drug upon immersion of the dosage form in fluid.

2. The method of claim 1 in which said solid matrix is a member selected from the group consisting of celluloses, substituted celluloses, microcrystalline cellulose, polysaccharides, substituted polysaccharides, polyl(alkylene oxide)s, poly(vinyl alcohol), starch, starch-based polymers, crosslinked poly(acrylic acid)s, and substituted crosslinked poly(acrylic acid)s.

3. The method of claim 1 in which said solid matrix is a member selected from the group consisting of poly(ethylene oxide), hydroxypropyl methyl cellulose, and combinations of poly(ethylene oxide) and hydroxypropyl methyl cellulose.

4. The method of claim 1 in which said polymeric film is a member selected from the group consisting of poly(ethylene oxide), hydroxypropyl methyl cellulose, polyvinyl alcohol, combinations of poly(ethylene oxide) and hydroxypropyl methyl cellulose, and combinations of polyvinyl alcohol and poly(ethylene oxide).

5. The method of claim 1 in which said fluid medium comprises a liquid solution of said first drug in a solvent.

6. The method of claim 1 in which said fluid medium comprises a liquid solution of said first drug and a polymer in a solvent.

7. The method of claim 1 in which said fluid medium comprises a suspension of said first drug in solid particle form in a liquid suspending agent.

8. The method of claim 1 in which said fluid medium comprises a suspension of said first drug in solid particle form and a dispersing agent, also in solid particle form, in a liquid suspending agent, said dispersing agent being a substance that separates into discrete particles upon contact with gastrointestinal fluid.

9. The method of claim 1 in which said fluid medium is an aqueous suspension of said first drug, and said first drug is comprised of particles having a weight-averaged diameter equal to or less than 25 microns.

10. The method of claim 1 in which said fluid medium is an aqueous suspension of said first drug, and said first drug is comprised of particles having a weight-averaged diameter equal to or less than 10 microns.

11. The method of claim 1 wherein the weight ratio of said polymeric film to said unitary body is from about 0.01:1 to about 0.1:1.

12. The method of claim 1 in which the weight ratio of said polymeric film to said unitary body is from about 0.01:1 to about 0.08:1.

13. The method of claim 1 in which (b) comprises surrounding said unitary body entirely with said polymeric film, and said solid layer of (d) is a shell completely encasing said unitary body and polymeric film.

14. The method of claim 1 in which (b) and (c) comprise depositing said polymeric film and said first drug over only a portion of the entire surface of said unitary body, leaving the remainder of said unitary body exposed.

15. The method of claim 1 in which said liquid carrier of step (c) is water.

16. The method of claim 1 in which said liquid carrier of step (c) is an organic solvent.

17. The method of claim 16 in which said organic solvent is a member selected from the group consisting of ethanol, hexanes, chloroform, carbon tetrachloride, and dimethyl sulfoxide.

* * * * *